(12) United States Patent
Park et al.

(10) Patent No.: US 7,217,855 B2
(45) Date of Patent: May 15, 2007

(54) GENE CONTROLLING FLOWERING TIME AND METHOD FOR CONTROLLING FLOWERING TIME IN PLANTS USING THE GENE

(75) Inventors: Don-Ha Park, Goyang-si (KR); Hong-Gil Nam, Pohang-si (KR); Pyung-Ok Lim, Pohang-si (KR)

(73) Assignees: Postech Foundation, Seoul (KR); Genomine, Inc., Pohang (KR)

( * ) Notice: Subject to any disclaimer, the term of this patent is extended or adjusted under 35 U.S.C. 154(b) by 238 days.

(21) Appl. No.: 10/487,220

(22) PCT Filed: Aug. 22, 2002

(86) PCT No.: PCT/KR02/01584

§ 371 (c)(1),
(2), (4) Date: Feb. 20, 2004

(87) PCT Pub. No.: WO03/018628

PCT Pub. Date: Mar. 6, 2003

(65) Prior Publication Data

US 2005/0183166 A1    Aug. 18, 2005

(30) Foreign Application Priority Data

Aug. 22, 2001  (KR) .............................. 2001-50773

(51) Int. Cl.
*C12N 15/82* (2006.01)
(52) U.S. Cl. .................... 800/278; 800/290; 800/320.1
(58) Field of Classification Search .............. 536/23.1, 536/23.6; 435/320.1, 410; 800/278, 298, 800/290, 320.1
See application file for complete search history.

(56) References Cited

U.S. PATENT DOCUMENTS 5,861,542 A * 1/1999 An ............................. 800/278
6,177,614 B1 * 1/2001 Colasanti et al. ........... 800/290

FOREIGN PATENT DOCUMENTS

KR   10-1999-0030639 A   5/1999
KR   10-2001-0029127 A   4/2001
WO       00/50615 A1      8/2000
WO       01/02572 A1      1/2001

OTHER PUBLICATIONS

Bowie et al, Science 247:1306-1310, 1990.*
McConnell et al, Nature 411 (6838):709-713, 2001.*
Kano-Murakami et al (1993, FEBS 334:365-368).*
Federspiel et al (Jul. 2000, NCBI Accession No. AC021043).*
NCBI Accession #NM 102657, "Dof-type zinc finger domain—containing protein [*Arabidopsis thaliana*]", Aug. 20, 2002.
Levy et al., "The Transition to Flowering," *The Plant Cell*, 1998, pp. 1973-1989, vol. 10, Amer. Soc. of Plant Physiologists, Rockville, MD.
Nilsson et al., "Flowering-Time Genes Modulate the Response to *LEAFY* Activity," *Genetics*, 1998, pp. 403-410, vol. 150 No. 1, Genetics Society of America, Bethesda, MD.
Reed et al., "Independent Action of ELF3 and phyB to Control Hypocotyl Elongation and flowering Time," *Plant Physiol.*, 2000, pp. 1149-1160, vol. 122 No. 4, Amer. Soc. of Plant Physiologists, Rockville, MD.
Swarup et al., "Natural allelic variation identifies new genes in the *Arabidopsis* circadian system," *Plant J.*, 1999, pp. 67-77, vol. 20 No. 1, Blackwell Sciences, Oxford, England.
Levy et al., "Control of flowering time", *Curr. Opin. Plant Biol.*, 1998, pp. 49-54, vol. 1 No. 1, Current Biology Ltd., London England.

* cited by examiner

*Primary Examiner*—Stuart F. Baum
(74) *Attorney, Agent, or Firm*—Buchanan Ingersoll & Rooney PC

(57) ABSTRACT

The present invention relates to a gene regulating flowering time and a method for regulating flowering time in plants using the same. More particularly, the present invention relates to a COG gene having nucleotide sequence represented by SEQ ID No: 1 which is isolated from *Arabidopsis thaliana*, and a method for delaying flowering time of plants by overexpressing the gene, or for inducing early flowering by repressing an expression of the gene. The COG gene and the COG protein expressed therefrom according to the present invention are useful for improvement of flowering-associated character of plants, and for identification of flowering-associated genes or proteins in other plants, etc.

3 Claims, 6 Drawing Sheets

SEQUENCE LISTING

```
<160> NUMBER OF SEQ ID NOS: 6

<210> SEQ ID NO 1
<211> LENGTH: 540
<212> TYPE: DNA
<213> ORGANISM: Arabidopsis thaliana

<400> SEQUENCE: 1
ttttaatggc gacccaagat tctcaaggga ttaaactctt tggcaaaacc ataacattca      60
acgccaacat cacacagacg ataaaaaaag aagagcagca acaacaacaa cagccagagc     120
tacaagcaac aacagccgtt agatcaccct catcggatct gacggctgag aagcgtccag     180
acaagatcat accatgtccg agatgcaaga gcatggagac taagttttgt tacttcaaca     240
actacaacgt taatcaacca agacacttct gcaaaggttg tcaacgttac tggaccgccg     300
```

-continued

```
gtggagctct ccggaatgtt cccgtcggtg ccggtcgtcg gaagtcaaaa cctcccggac    360
gtgtcggtgg gttcgctgag ttgcttggag ctgcgactgg agctgttgat caggtcgagc    420
tagatgcttt gctagtggaa gagtggagag ctgctacggc gtctcacggt ggtttccggc    480
atgattttcc ggtgaagagg ctccgttgtt acaccgatgg tcaatcttgt taattatttt    540
```

<210> SEQ ID NO 2
<211> LENGTH: 175
<212> TYPE: PRT
<213> ORGANISM: Arabidopis thaliana

<400> SEQUENCE: 2

```
Met Ala Thr Gln Asp Ser Gln Gly Ile Lys Leu Phe Gly Lys Thr Ile
  1               5                  10                  15

Thr Phe Asn Ala Asn Ile Thr Gln Thr Ile Lys Lys Glu Glu Gln Gln
             20                  25                  30

Gln Gln Gln Gln Pro Glu Leu Gln Ala Thr Thr Ala Val Arg Ser Pro
         35                  40                  45

Ser Ser Asp Leu Thr Ala Glu Lys Arg Pro Asp Lys Ile Ile Pro Cys
     50                  55                  60

Pro Arg Cys Lys Ser Met Glu Thr Lys Phe Cys Tyr Phe Asn Asn Tyr
 65                  70                  75                  80

Asn Val Asn Gln Pro Arg His Phe Cys Lys Gly Cys Gln Arg Tyr Trp
                 85                  90                  95

Thr Ala Gly Gly Ala Leu Arg Asn Val Pro Val Gly Ala Gly Arg Arg
            100                 105                 110

Lys Ser Lys Pro Pro Gly Arg Val Gly Gly Phe Ala Glu Leu Leu Gly
        115                 120                 125

Ala Ala Thr Gly Ala Val Asp Gln Val Glu Leu Asp Ala Leu Leu Val
    130                 135                 140

Glu Glu Trp Arg Ala Ala Thr Ala Ser His Gly Gly Phe Arg His Asp
145                 150                 155                 160

Phe Pro Val Lys Arg Leu Arg Cys Tyr Thr Asp Gly Gln Ser Cys
                165                 170                 175
```

<210> SEQ ID NO 3
<211> LENGTH: 31
<212> TYPE: DNA
<213> ORGANISM: Artificial Sequence
<220> FEATURE:
<223> OTHER INFORMATION: 5' primer for PCR of COG gene

<400> SEQUENCE: 3

```
atttccatgg cgacccaaga ttctcaaggg a                                    31
```

<210> SEQ ID NO 4
<211> LENGTH: 30
<212> TYPE: DNA
<213> ORGANISM: Artificial Sequence
<220> FEATURE:
<223> OTHER INFORMATION: 3' primer for PCR of COG gene

<400> SEQUENCE: 4

```
tcggggtgac cttaacaaga ttgaccatcg                                      30
```

<210> SEQ ID NO 5
<211> LENGTH: 30
<212> TYPE: DNA
<213> ORGANISM: Artificial Sequence
<220> FEATURE:

-continued

```
<223> OTHER INFORMATION: 5' primer for PCR of COG gene

<400> SEQUENCE: 5
tacccgggca atggcgaccc aagattctca                               30

<210> SEQ ID NO 6
<211> LENGTH: 34
<212> TYPE: DNA
<213> ORGANISM: Artificial Sequence
<220> FEATURE:
<223> OTHER INFORMATION: 3' primer for PCR of COG gene

<400> SEQUENCE: 6
cgtagtcgac ttaacaagat tgaccatcgg tgta                          34
```

GENE CONTROLLING FLOWERING TIME AND METHOD FOR CONTROLLING FLOWERING TIME IN PLANTS USING THE GENE

TECHNICAL FIELD

The present invention elates to a gene controlling flowering time and a method for controlling flowering time in plants using the gene. More particularly, the present invention relates to a COG gene having nucleotide sequence represented by SEQ D No: 1 which is isolated from *Arabidopsis thaliana*, and a method for delaying flowering time of plants by overexpressing the gene, or for inducing early flowering by inhibiting the expression of the gene.

BACKGROUND OF THE INVENTION

Flowering time in plants varies greatly depending on temperature, the duration of daylight (photoperiod), or both. Generally, according to the relationship between the photoperiod and the flowering time, plants are largely divided into three classes; i.e., long daylight plant which flowers under long daylight, short daylight plant which flowers under short daylight, or day-neutral plant which flowers independent of daylight Such flowering characteristic is believed to be under the basic control of several genes (Yaron Y. Levy and Caroline Dean (1998) *The Plant Cell*, 10: 1973–1989).

Many studies have been carried out to examine various kinds of mutants, genes, or a pathway controlling the flowering, which affect the flowering time in plants. As a result, it is found that there are three pathways controlling the flowering in *Arabidopsis thaliana*, of which flowering is stimulated under long daylight The first pathway is an autonomous pathway, in which the flowering is controlled with no connection with the duration of daylight For this pathway, genes of LD, PGM1, FY, FCA, FPA, FLD, etc. are found to be related thereto (Chentao Lin, *Plant Physiology*, 123: 39–50, 2000). The second pathway is a photoperiodic pathway, in which the flowering in plants is controlled by sensing the duration of daylight Genes of ELF3, CAM1, GI, CO, FWA, FT, FE, etc. are known to play an important role in this pathway (Yaron Y. Levy and Caroline Dean (1998), *The Plant Cell*, 10: 1973–1989). The third pathway is a vernalization pathway, in which the flowering is controlled by temperature. In this pathway, the flowering of plants is simulated by their exposure to low temperature for a certain period of time. Relating genes of VRN1, VRN2, FRI, FLC, etc. were isolated.

Meanwhile, flowering time is important in crops. For green leaf vegetables such as lettuce, spinach, and dropwart, etc., their leaves quickly become aged after the flowering, and therefore their market value is significantly lowered. Grain crops are divided into three varieties depending on their growth time from sowing to flowering, i.e., early variety, medium variety, and late variety. Early variety yields relatively a low amount of harvest due to its short growth time, but it is advantageous in that it can be harvested early or on the market early. For these and other reasons, flowering time has been the important subject of classic breeding in agriculture.

The breeding method used in classic breeding is typically a cross-breeding method. However, according to this method, it is impossible to introduce specifically one or two genes into a desired crop. As such, a group of unnecessary genes has to be removed in order to have only a character of the desired gene after the breeding, and thus to have the character fixed. To do so, it takes usually a long period of time of 5 to 20 years and lots of efforts. Further, the resulting crop variety which is fixed according to the above method still can display recessive character or sensitivity to pathogenes that have not been considered during the process of breeding and therefore causing a trouble after it is made available to the public. Since breeding to control the flowering time is also based on the conventional cross-breeding method, problems are present For example, instability of breed variety and excessive amounts of time and efforts required therefor, etc. Recently, however, it is possible to isolate genes related to the control of flowering time and to utilize them in breeding with appropriate manipulation of the genes, all thanks to the development in genetic engineering technology. In results, it is expected to have new breed varieties of which flowering time is either artificially controlled or can be possibly controlled (Ove Nilson and Detlef Weigle, *Current Opinion in Biotechnology*, 8: 195–199, 1997). In this connection, studies have been carried out to isolate a gene inducing mutation from a mutant which expresses a phenotype of eloped flowering time. For example, flowering-controlling genes such as OsMADS5~8, MdMADS3 and MdMADS4 are disclosed in the publication of Korean patent application No. 1999-0030639, and GIGANTEA gene which controls flowering time and biological clock in *Arabidopsis thaliana* is disclosed in the publication of Korean patent application No. 2001-0029127. However, taken together the study results up to the present, it is believed that the control of flowering time in plants involves quite complicated pathways and various genes (Alon Samach and George, *Coupland BioEssays*, 22: 38–47, 2000). Therefore, studies on new genes controlling the flowering time in plants and functional studies therefor are required.

DETAILED DESCRIPTION OF THE INVENTION

The present invention is accomplished on the basis of the above described need in the pertinent field Thus the purpose of the present invention is to provide a gene controlling flowering time in plants.

Another purpose of the invention is to provide a method for controlling flowering time in plants using the above-mentioned gene.

In order to achieve such purposes, the present invention provides a COG gene having nucleotide sequence of SEQ ID No: 1 which controls the flowering time in plants.

Still, in order to achieve another purpose of the invention, the present invention provides a method for delaying flowering time in plants by over-expressing the COG gene in the plants transformed with the vector in which the said COG gene is inserted in sense direction, or for inducing early flowering by inhibiting the expression of the COG gene in the plants by transforming them with a vector m which the said COG gene is inserted in antisense direction.

Term a "flowering-delayed cog mutant" or a "cog mutant" represents mutants in which the COG gene is activated by activation tagging method so that the mutant plant has a phenotype of delayed flowering.

The present invention is described in detail herein below.

In the present invention, a mutant which expresses delayed flowering phenotype is selected in order to screen genes related to the control of flowering time. *Arabidopsis thaliana* is adopted as the test subject in the present invention, which is widely used as a study material in plant genetics and molecular biology. There are three major methods of inducing mutation used in the pertinent art to identify gene function First method is a chemical method to treat with chemicals such as EMS (ethyl-methyl sulfonic acid), etc. Second method is to irradiate X-ray or gamma ray, and therefore causing a mutation. Third method is to use T-DNA of *Agrobacterium*, which is soil bacteria, for inducing mutation via transformation therewith Said methods involving the treatment with chemicals, X-ray or gamma-ray irradiation, or inserting T-DNA to induce mutation are based on the principle that by the said treatments a part of or the entire gene is degraded and the function of the corresponding gene is lost, and therefore its function can be deduced. However, mutations caused by such methods are generally recessive ones, and when a gene functionally similar to the degraded gene is additionally present in the genome of the subject, the phenotype corresponding to the degraded gene may not appear due to the presence of the said similar gene. In addition, when the degraded gene is functionally very important, it can cause lethality in plant.

On the other hand, according to the activation tagging method used in the present invention, T-DNA activates expression of plant genes without degrading their DNA sequences. As such, even if functionally similar or overlapped gene is present on the same genome of *Arabidopsis thaliana*, the corresponding phenotype can be still induced (Weigel et al., *Plant Physiology* 122:1003–1014, 2000). More specifically, said activation tagging method uses an activation tagging vector, which comprises a selection marker in T-DNA for easy separation of other DNAs near T-DNA, a replication origin required for the replication in *E. coli*, and an ampicillin-resistant gene. Furthermore, the activation tagging vector has four 35S CaMV enhancers m the right border of T-DNA. Therefore, when T-DNA is inserted into a genome of plants, it activates genes around sites inserted with the T-DNA, thereby inducing, mutations (see FIG. 2). In this case, even when a functionally similar gene is presenting the genome, the corresponding phenotype can be expressed by the genes activated by the enhancers. As a result, if the above-mentioned activation tagging method is applied to determine flowering controlling genes in plant, it is highly likely that new flowering controlling genes which are not identified by the "loss of function" mutation method can be found. In addition, the activation aging method has another advantage of inducing dominant mutation, and accordingly the phenotype caused by the mutation can be observed one generation early. In this connection, the present inventors investigated the genes related to the control of the flowering time in plants by means of screening flowering-delayed mutants of *Arabidopsis thaliana* produced by the activation tagging method.

In one embodiment of the present invention, in order to select the *Arabidopsis thaliana* mutants with delayed flowering, mutants are prepared using the activation tagging vector pSK1015, and then the mutant with the delayed flowering is selected from the grown plants via an eye measurement Thus, the obtained mutant is named "cog mutant." Then, to confirm the phenotype of delayed flowering, when the flower stalk is formed and becomes about 3 cm long (bolting time), the flowering time is determined based on the number of rosette leaves. As a result, it is found that, compared to the wild type, the number of rosette leaves increases in the flowering-delayed cog mutant under the long daylight condition which stimulates the flowering (see FIG. 1). This result demonstrates that the extended period for vegetative growth causes the delay m the flowering.

In another embodiment of the present invention, genes relating to the control of the flowering in plants are isolated from the above-described cog mutant, using the plasmid rescue method (Weigel et al., *Plant Physiology* 122:1003–1014, 2000). Then, the nucleotide sequence is determined for the DNA fragment around the T-DNA insertion region, which is isolated via said plasmid rescue method. The nucleotide sequence obtained therefrom is compared to the *Arabidopsis thaliana* genome database. Accordingly, the open reading frame which resides most closely to the enhancer is found. It is confirmed that the resulting gene consists of a single exon, with 540 bp encoding 175 amino acids. The gene is named 'COG.' A nucleotide sequence of the COG gene is listed in SEQ ID: NO 1.

The peptide sequence deduced from the nucleotide sequence of the above-identified COG gene is studied using the database. It is found that the protein expressed from the said COG gene consists of 175 amino acids and has a molecular weight of 19 kDa (SEQ ID: NO. 2). According to the peptide sequence analysis of the COG protein using the computer program for the prediction of protein localization (PSORT; psort.nibb.ac.jp), it is found that the amino acid sequence known as DOF (DNA binding with one finger) and commonly shared among transcription factors is conserved (see FIG. 3). Genes containing DOF domain are a group of genes specifically found in plants. They are known as a transcription factor related to various physiological phenomena such as activation of genes associated with photosynthesis, genes of seed storage protein, genes induced by plant hormone, stress inducing genes and plant oncogenes, etc. (Yanagisawa, *Trends in Plant Science*, 1:213–214, 1996).

Yet, in another embodiment of the present invention, Northern blot analysis is carried out using the above-described COG gene as a probe, in order to find out whether the phenotype of flowering delay appearing in the cog mutant is caused by the activation of COG gene or not Consequently, it is found that the COG gene is not expressed in the wild type but overexpressed in the cog mutant (see FIG. 4). Moreover, the COG gene is reintroduced into the wild type of *Arabidopsis thaliana*, and it is determined whether the phenotype of flowering delay appears again or not To do so, a recombinant vector in which the above-described COG gene is introduced in sense direction is constructed and named 'pGTE-COG.' *E. coli* strain transformed with this recombinant vector pGTE-COG was deposited with the Korean Collection for Type lures on Aug. 8, 2001 (Accession No: KCTC 10033BP). The wild type *Arabidopsis thaliana* is transformed with the pGTE-COG and the delay in flowering is determined for the transformants. As a result, it is confirmed that the delayed flowering phenotype also appears in the transformants as in the cog mutant Therefore, it is found that the delayed flowering phenotype in the cog mutant is caused by the activation of the COG gene, and thereby the delayed flowering can be induced by the activation of the COG gene in plants.

From the sequence analysis of the protein from the COG gene according to the present invention, it is discovered that a sequence usually found in transcription factors is also present in the amino acid sequence of the protein. As such, the COG protein expressed from the COG gene is considered as a transcription factor which regulates the gene expression in a nucleus. To confirm this, the present inventors investigated whether the COG protein migrates into the nucleus. Specifically, the said COG gene is fused to the gene of Green Fluorescence Protein (GFP) and then introduced into epidermal cells of onion via the particle bombardment method The expression of GFP-COG fusion protein is observed under the fluorescence microscope. GFP-COG protein is only detected in the nucleus. Such result is in agreement with the prediction result obtained from the computer program for the prediction of protein localization. Thus, it is highly likely that the protein encoded by COG gene of the present invention is in fact a transcription factor (see FIG. 5).

Furthermore, in order to determine whether the wild type early flowers when the expression of COG gene is intentionally inhibited in plant cells, the present inventors constructed a new recombinant vector in which the said COG gene is inserted in antisense direction. After transforming the wild type *Arabidopsis thaliana* with the said recombinant vector, the flowering time is monitored As a result, it is found that the early flowering occurs in the transformants with the inhibited expression of COG gene but not in the wild type *Arabidopsis thaliana* (see FIG. 6). This result demonstrates that the early flowering in plants can be induced by inhibiting the expression of COG gene.

Plants of which flowering time can be controlled by the method of the present invention include: food crops such as rice, wheat barley, corn, bean, potato, red bean, oat and millet; vegetable crops such as *Arabidopsis*, Chinese cabbage, radish, red pepper, strawberry, tomato, watermelon, cucumber, cabbage, melon, squash, stone-leek onion, and carrot; special crops such as ginseng, tobacco, cot, sesame, sugar cane, sugar beet, wild sesame, peanut, and rape; fruits such as apple, pear, date, peach, western Actinidia, grape, orange, persimmon, plum, apricot and banana; flowers such as rose, gladiolus, gerbera, carnation, mum, lily and tulip; fodder crops such as ryegrass, red clover, orchard grass, alfalfa, tail fescue and perennial ryegrass. Especially, the method of the present invention would be commercially very valuable when it is applied to green vegetables such as lettuce or spinach of which green leaves get quickly aged after the flowering, thereby causing deterioration in value of goods.

Further, COG gene and COG protein of the present invention can be useful for improving flowering-associated character of plants and for identifying flowering-associated genes and proteins in other plants. Especially, they can be used for identifying components associated with the flowering control in plants by identifying components binding to the genes or proteins of the present invention and inhibiting or activating the expression of the above-mentioned COG gene. More specifically, the identification can be carried out by various methods including DNA chip, protein chip, PCR, Northern blot analysis, Southern blot analysis, Western blot analysis, ELISA, 2-D gel analysis, etc.

BRIEF DESCRIPTION OF THE DRAWINGS

1, 10: DOF domain sequences found in the corn proteins
2, 4, 6~9, 12~18: DOF domain sequences found in the proteins of *Arabidopsis thaliana*
3: DOF domain sequence of the COG protein according to the present invention
5: DOF domain sequence found in a cucumber

BEST MODE FOR CARRYING OUT THE INVENTION

The present invention will hereinafter be described in further detail by examples. It should however be borne in mind that the present invention is not limited to or by the

EXAMPLE 1

Selection of Flower-delayed Mutant from *Arabidopsis thaliana*

First, to induce a mutation for *Arabidopsis thaliana*, pSK1015 (Weigel et al., *Plant Physiology*, 122:1003–1014, 2000; acquired from Weigel laboratory, US), an activation tagging vector, was introduced into an *Agrobacterium tumefacience* ABI strain (acquired from Amasino Laboratory, US) by electroporation An *Agrobacterium tumefacience* strain inserted with pSK1015 vector was selected in medium containing kanamycin and carbenicillin. Then, Columbia, the wild type *Arabidopsis thaliana*, were transformed with the selected *Agrobacterium tumefacience* strain according to the floral dip method (Clough et al., *Plant J.*, 16(6):735–743, 1998). Transformants resistant to herbicide were selected from seeds originated from the transformed *Arabidopsis thaliana*. Then, 5000 of the T1 lines were grown in a greenhouse adjusted to the temperature of about 23° C., and flowering-delayed mutants were observed with the naked eyes. One line of mutant late in flowering time was selected compared with wild type, and then the flowering-delayed mutant was named "cog mutant".

EXAMPLE 2

Figure 1:
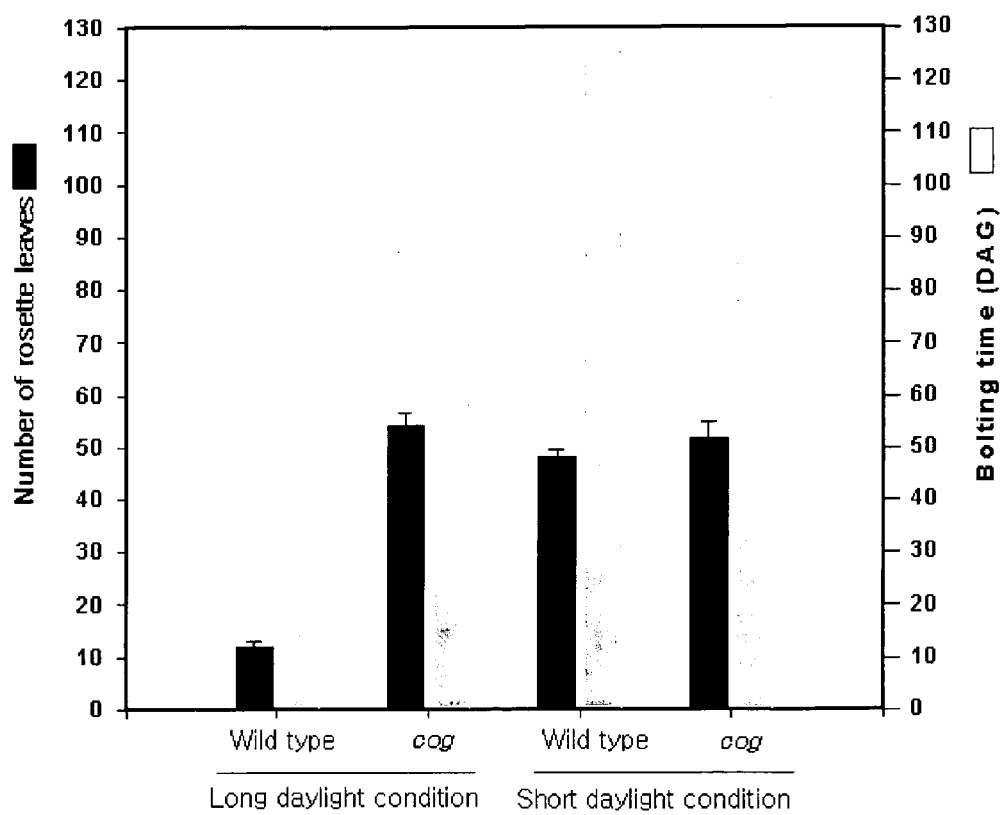
FIG. 1 represents the flowering times for wild type and flowering-delayed cog mutants of *Arabidopsis thaliana*, under the long daylight or the short daylight

Comparison of the Flowering Time Between the Wild Type *Arabidopsis thaliana* and a Flowering-delayed Mutant The flowering time of the cog mutant selected in Example 1 was compared with that of the wild type *Arabidopsis thaliana*, under the condition that the number of rosette leaves when flower stalks were formed and their length were about 3 cm (bolting time) were taken as an indication for the start of flowering time. First seeds from the wild type *Arabidopsis thaliana* and the cog mutant were vernalized for about 3–5 days at 4° C., so that all seeds were allowed to germinate at constant time by adjusting cell cycles of the embryo in seeds cons Thereafter, the vernalized seeds were seeded in pot at regular intervals. After seeding, wet condition with the pot wrapped was maintained for about 7 days to support the germination of seeds. When seeds were germinated, the pot was transferred to the condition that long daylight condition consists of daytime for 16 hours and night for 8 hours, and short daylight condition consists of daytime for 8 hours and night for 16 hours, seeds were grown until the length of flower stalks is about 3 cm, and then the number of rosette leaves was examined As a result, as shown in FIG. 1, in case of a cog mutant, the number of rosette leaves creased compared with that of the wild type in the long daylight condition of promoting flowering, and late-flowering was observed at the same time. Such late-flowering showed the similar flowering to that in long daylight condition This indicates that the flowering time of cog mutant is delayed compared with that of the wild type as its vegetative growth period gets longer.

EXAMPLE 3

Cloning and Sequence Analysis of a COG Gene

Figure 2:
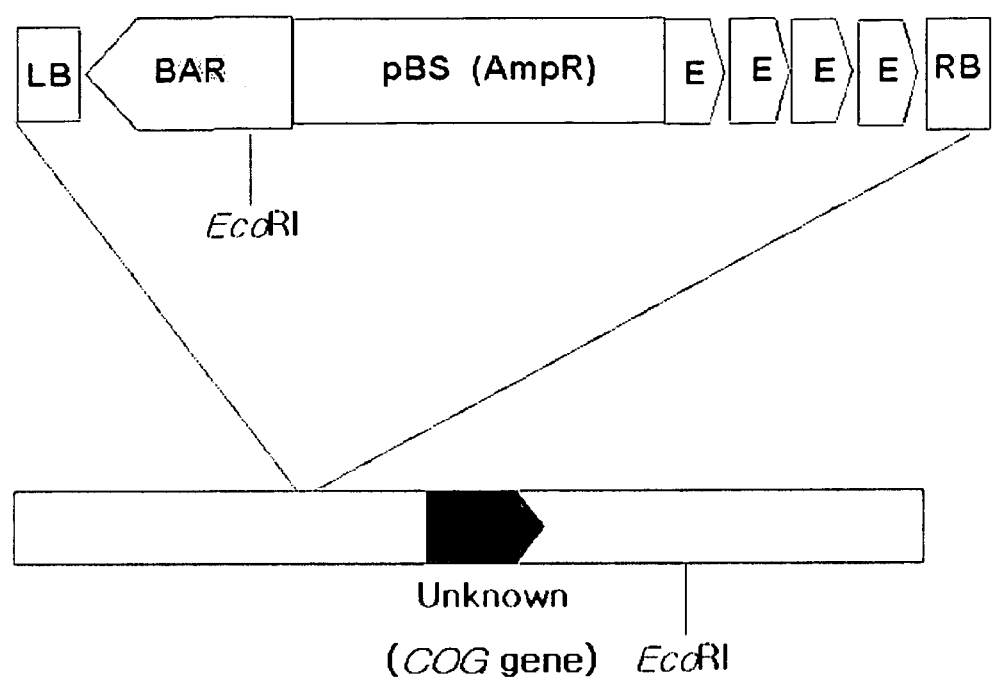
FIG. 2 is a diagram of activation tagging vector pSKI105 inserted into a genome of flowering-delayed cog mutant
E: an enhancer
BAR: a herbicide-resistant gene
pBS: a region containing a replication origin of *E. coli* and an ampicillin-resistant gene
Figure 3:
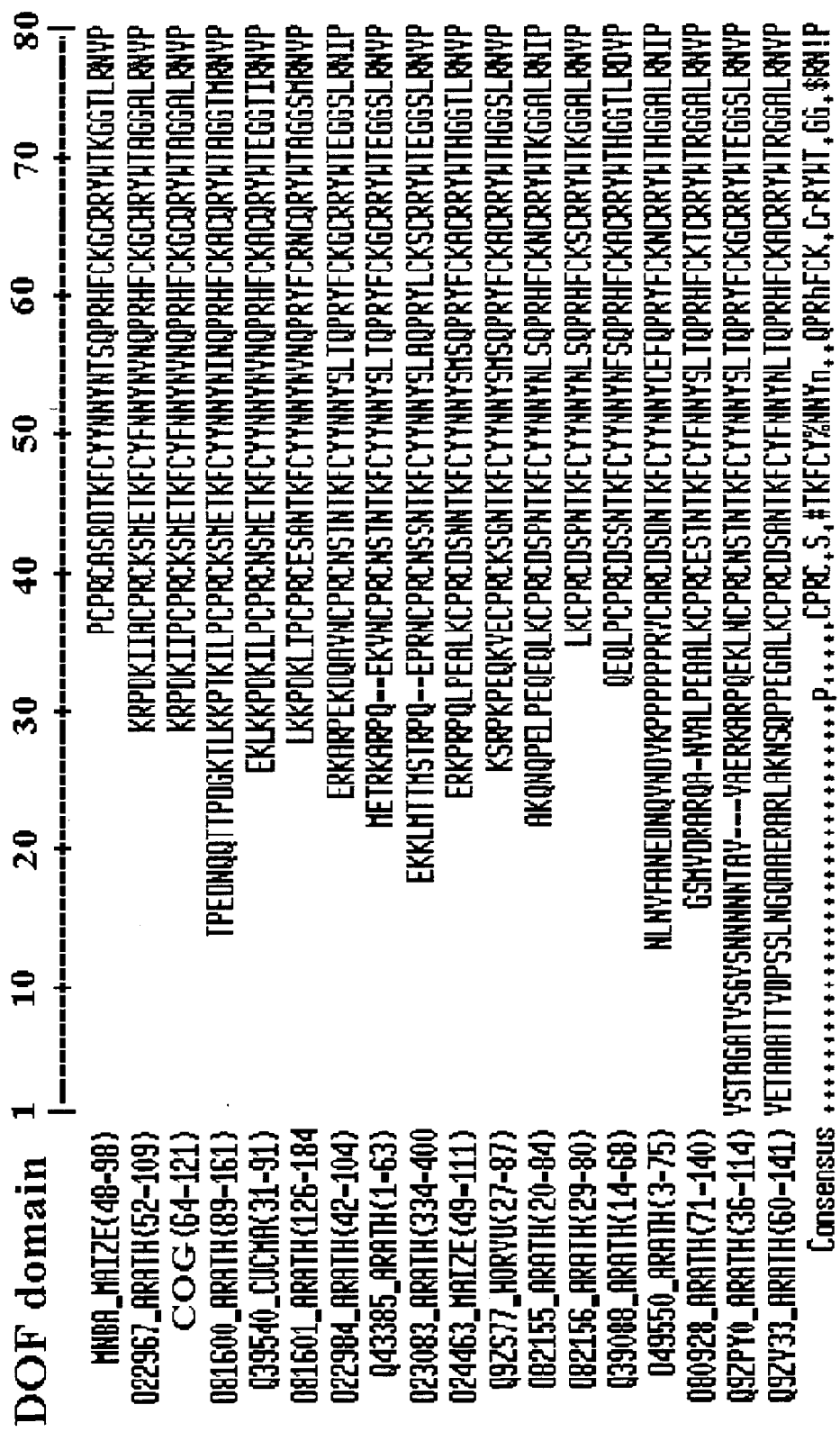
FIG. 3 shows the comparison between the DOF domain sequence which is conserved in the ammo acid sequence of COG protein of the present invention and DOF domain sequence of the proteins in other species which also include DOF domain (SEQ ID NOS:7–25).

To screen a plant gene around T-DNA activated by enhancer in cog mutant, a gene around TDNA was isolated according to the plasmid rescue method (Weigel et al., *Plant Physiology* 122:1003–1014, 2000). FIG. 2 depicts a diagram that activation tagging vector pSKI015 is integrated into the genome of the cog mutant with delayed flowering. First, the entire genomic DNA was isolated according to the method of Dellaporta et al. from a cog mutant (Dellaporta et al., *Plant Mol. Biol. Rep.* 1:19–21, 1983). Then, 5 µg of genomic DNA was digested with EcoRI restriction enzyme, precipitated with ethanol, and then dried. The digested DNA was self-ligated, and then DH5α was transformed with the ligated DNA. Thereafter, colonies resistant to ampicillin were selected. A plasmid was isolated from the selected colonies according to the known method, the nucleotide sequence of region 4.0 kb away from T-DNA right border was determined and analyzed using the oligomer prepared based on the nucleotide sequence of EcoRI site downstream used for the plasmid rescue method. The determined nucleotide sequence was searched for the genome database of *Arabidopsis thaliana*, and then an open reading frame nearest from enhancer was found. The isolated open reading frame was named the "COG gene", and its nucleotide sequence is listed in the SEQ ID: No. 1. As described in SEQ ID: No. 2, the protein expressed from the COG gene consists of 175 amino acids, and its molecular weight is 19 kDa. As a result of analyzing the protein sequence using computer program for the prediction of protein localization (PSORT; psort.nibb.ac.jp), it was found that a DOF domain is present in the region of amino acids 64~421 of the SEQ ID: No. 2. FIG. 3 shows the comparison between DOF domain sequence conserved in the amino acid sequence of the COG gene according to the present invention and DOF domain sequence of the proteins in other species containing the DOF domain.

EXAMPLE 4

Comparison of the COG Gene Expression Between Wild Type *Arabidopsis thaliana* and a cog Mutant To confirm that the COG gene isolated in Example 3 is over-expressed in a cog mutant but not in wild type *Arabidopsis thaliana*, the Northern blot analysis was carried out with the COG gene as a probe. RNA was isolated from wild type *Arabidopsis thaliana* and the cog mutant respectively, using Tri-reagent (Sigma), according to the method of Woo et al. (Woo H. R. et al., *Plant Cell,* 13:1779–1790, 2001). 10 µg RNA in each lane was loaded and separated on 1.2% agarose/formaldehyde gel, and then transferred to nylon membrane. Then, the membrane was washed with 3×SSC for 5 minutes, the remaining agarose was removed, and then ultraviolet light (254 nm, 0.18 J/cm$^2$) was irradiated to fix RNA on the nylon membrane. The blot transferred to the nylon membrane was subjected to prehybridization and hybridization reaction according to the method of Park et al. (Park et al., *Plant Mol. Biol.* 26:1725–1735, 1994).

Figure 4:
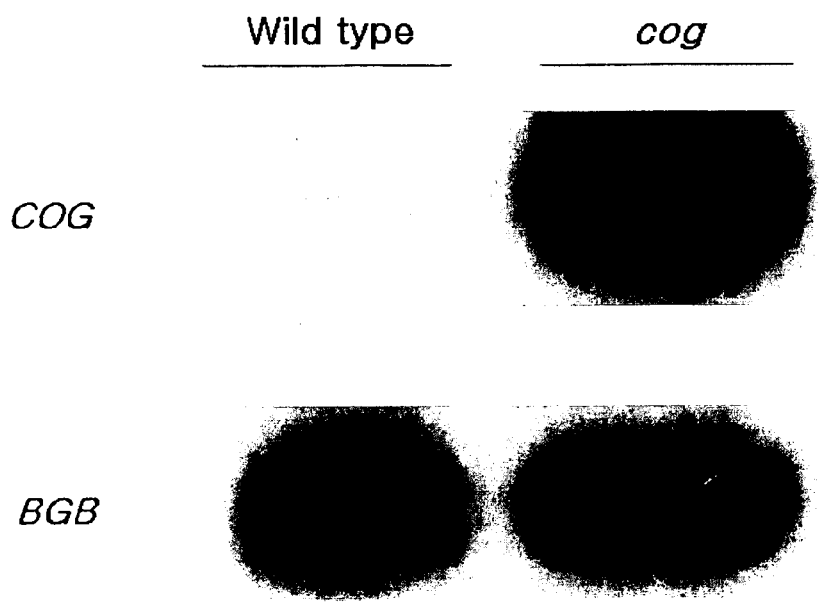
FIG. 4 shows the expression of the COG gene m wild type and the flowering-delayed cog mutant of *Arabidopsis thaliana*. The results are obtained from Northern blot analysis. BGB represents an internal control.

As a result, as shown in FIG. 4, it is confirmed that COG gene expression is very high in the cog mutant while it is almost negligible in the wild type.

EXAMPLE 5

Transformation of a COG Gene Into a Wild Type *Arabidopsis thaliana*

To finally confirm whether a flowering-delayed phenotype appearing in a cog mutant is due to the activation of a COG gene, a recombinant vector was constructed by the following method such that the COG gene is overexpressed in wild type *Arabidopsis thaliana*.

First, the region containing the entire COG gene was isolated by PCR To make cloning easy, each pruner was prepared by inserting Nco I site for a forward primer and BstEII site for a reverse primer Then, PCR was carried out using genomic DNA of the wild type *Arabidopsis thaliana* as a template using the forward primer of SEQ ID: No. 3 and the reverse primer of SEQ ID: No. 4. PCR condition was as follows: heat-denatured for 5 min at 95° C., amplified by repeating 35 cycles for 0.5 min at 94° C., 0.5 min at 55° C. and 1 min at 72° C., and then the reaction was completed 0.54 kb of DNA fragment obtained from the above PCR reaction was separated by agarose gel electrophoresis, cloned into GEM T easy vector (Promega, US), and named "pGTE-COG". *E. coli* DH5 α was transformed with the pGTE-COG vector. The transformed *E. coli* DH5α was deposited with Korean Collection for Type Cultures on Aug. 8, 2001 (Accession number: KCTC 10033BP).

Then, the COG gene of the present invention was isolated from the recombinant vector using Nco I and BstE II, inserted into pCAMBIA3301 vector (MRC, US) for plant transformation, and named "pCOG-3301".

Then, the wild type *Arabidopsis thaliana* was transformed with the pCOG-3301 vector according to the floral dip method (Clough et al., *Plant J.,* 16(6): 735–743, 1998).

Thereafter, a transfomant resistant to herbicide was selected at obtaining seeds from the transformed *Arabidopsis thaliana*. Then, as a result of observing delayed flowering phenomenon with the selected transfomant cultured in a growth chamber, it is confirmed that a flowering-delayed phenotype observed in the cog mutant appeared again. From this, it is confirmed that the delayed flowering phenotype in a cog mutant appears by means of activation of a COG gene, and also delay in flowering is induced by activating the COG gene in plants.

EXAMPLE 6

Expression Study of the GFP-COG Fusion Protein in Onion Epidermal Cell

As a result of searching the polypeptide sequence deduced from the nucleotide sequence of the COG gene as determined in Example 3 from database, the presence of DOF domain sequence was confirmed. The DOF domain is found among transcription factors controlling expression of other genes in a nucleus. Therefore, the present inventors tried to confirm whether the COG protein of the present invention migrates into a nucleus.

First a gene encoding entire COG protein was amplified by PCR with the primers of SEQ ID: No. 5 and SEQ ID: No. 6 in the same method as described in Example 4. PCR-amplified DNA was inserted into the Sma I and HindIII site of 326 GFP-3G plasmid containing GEP (acquired from Prof In-Whan Hwang at Pohang University of Science and Technology) to construct a recombinant plasmid The resulting plasmid was named "pGFP-COG". Then, the expression of GFP-COG fusion protein was observed in the onion epidermal cell according to the method of Varagona et al. (Varagona et al, *Plant Cell*, 4:1213–1227, 1992). First, to coat a tungsten particle with DNA, A GFP-COG fusion protein-expressing plasmid was purified by Qiagen column. 2 μg of the plasmid DNA was precipitated with a tungsten particle in solution (Sigma) containing 50 μl of 2.5M $CaCl_2$ and 20 μl of 0.1M spermidine. The precipitate was washed with 70% ethanol, and then resuspended in 36 μl of 100% ethanoL The particle bombardment was carried out using the M-25 tungsten particle coated with the pGFP-COG DNA (Bio-Rad; Sanford et al., *Methods Enzymol.* 217:483–509, 1993) with 1350 p. s. i.(Biorad) after the bark of internal epidermal cell of onion is placed on ½ B5 media up. Then, the petri dish containing the above-obtained cells was sealed with parafilm, and then kept in an incubator at 22° C. for 18 hours. After 18 hours, GFP expression was observed with a fluorescence microscope.

Figure 5:
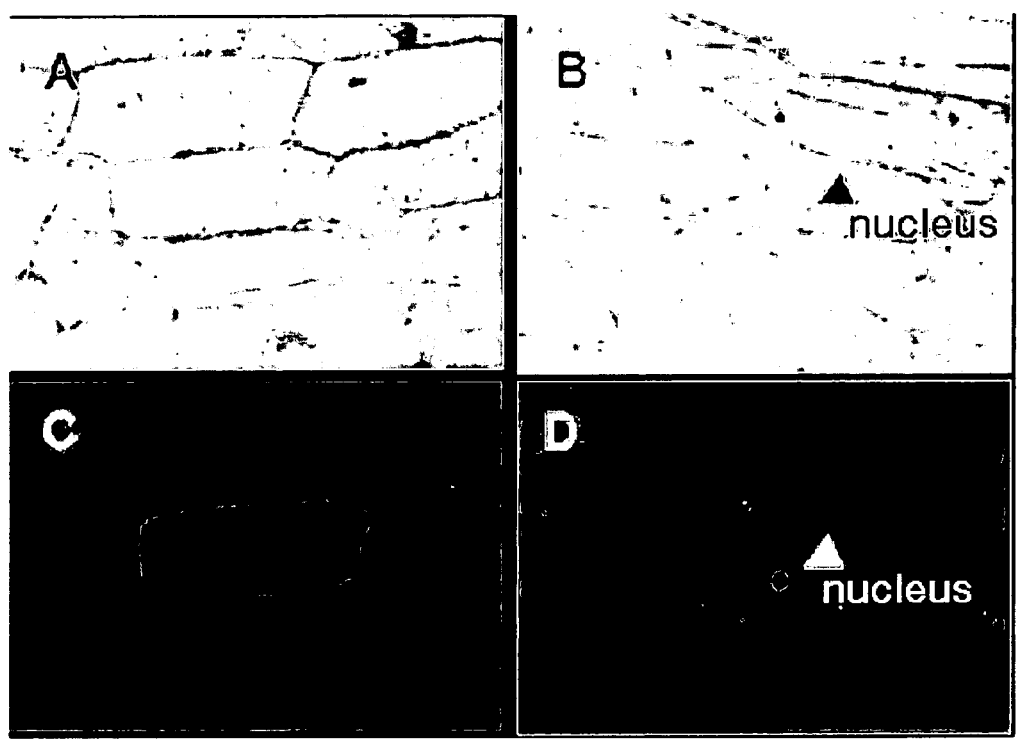
FIG. 5 is a micrograph showing the migration of GFP-COG fusion protein to a nucleus in an epidermal cell of onion.
A: 35S-GFP (positive internal control) observed with optical microscope
B: 35S-GFP-COG observed with optical microscope
C: 35S-GFP (positive internal control) observed with fluorescence microscope
D: 35S-GFP-COG observed with fluorescence microscope

As a result, as shown in FIG. 5, it is confirmed that the GFP-COG is expressed inside the nucleus. This indicates that the COG protein migrates to a nucleus and functions inside the nucleus.

EXAMPLE 7

Induction of the Early Flowering in Wild Type *Arabidopsis thaliana* Using the COG Gene By confirming that the COG gene over-expressing transfomant has a similar flowering time to the cog mutant in Example 5, the present inventors demonstrated that the late-flowering of the mutant is due to the overexpression of the COG gene, but not to the effect of transformation. Therefore, in o to confirm early flowering for the transformant in which the expression of the COG gene is inhibited compared to the wild type, the experiment is carried out to artificially inhibit the expression of COG gene by introducing the COG gene in antisense direction in cell; ie., a recombinant vector was constructed in which the COG gene was inserted in antisense direction. First to isolate the COG gene, pGTE-COG recombinant vector inserted with the COG gene was digested with NotI, and then inserted into NotI site of pNB96 (Pohang University of Science and Technology, *Planta*, 2001, in press) to construct a recombinant vector. Thereafter, a recombinant vector inserted with the COG gene in antisense direction was selected, and named "pCOC/AS-NB96". The wild type *Arabidopsis thaliana* was transformed with pCOG/AS-NB96 according to the same method as Example 5. Then, a flowering time of the transformant was observed in the same long daylight condition as Example 2.

Figure 6:
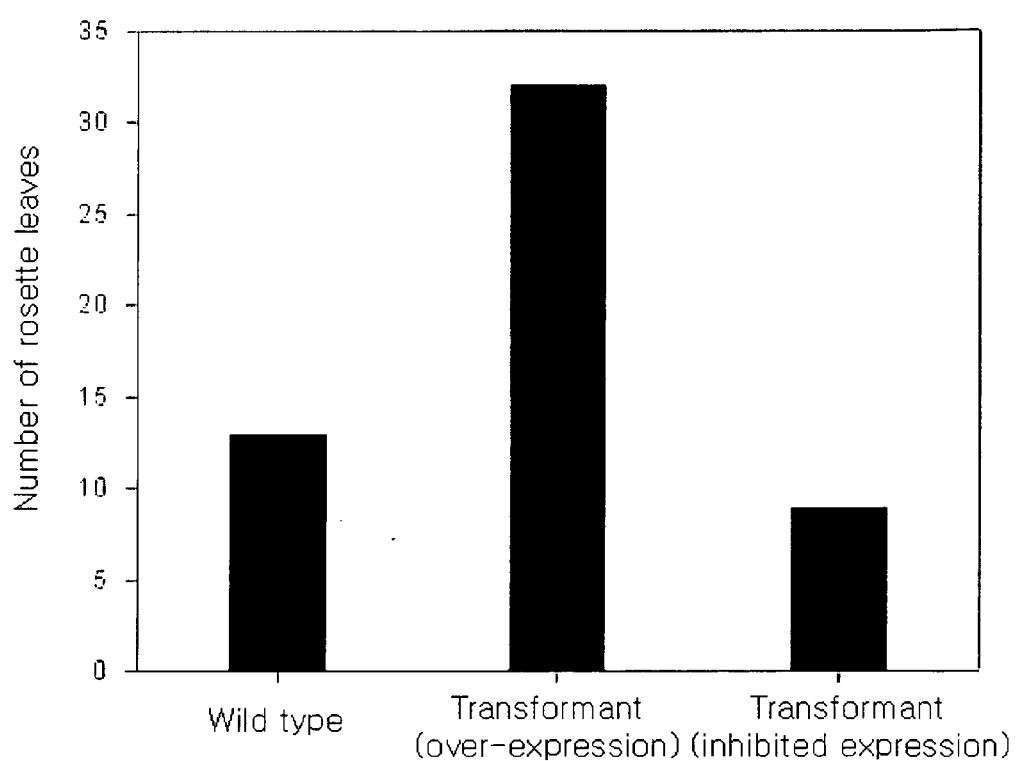
FIG. 6 shows the flowering time for the transformant having the COG gene of the present invention overexpressed, or for the transformant having the COG gene with inhibited expressions.

As a result, as shown in FIG. 6, it is confirmed that flower stalks were formed when the number of rosette leaves is 13–14 in the wild type *Arabidopsis thaliana*, while they were formed when the number of rosette leaves is 9–10 in the transformant in which the expression of the COG gene is artificially inhibited This result supports that an early flowering can be induced in plants by inhibiting the expression of the COG gene of the present invention.

INDUSTRIAL APPLICABILITY

As described in the above, it is confirmed in the present invention that the phenotype of delayed flowering in the cog mutant appears via activation of the COG gene, and the delaying or inducing a flowering time can be achieved by overexpressing said COG gene introduced in plant cells or by inhibiting its expression, respectively. The COG gene and the COG protein expressed therefrom according to the present invention are useful for improvement of flowering-associated characters of plants, and for identification of flowering-associated genes or proteins in other plants, etc. In addition, by inducing early flowering and dwarfing in plants using the COG gene of the present invention, the growth time can be reduced while harvest amount of crops is increased.

What is claimed is:

1. A method for controlling flowering time in plants comprising transforming a plant with an isolated polynucleotide encoding a COG protein which has the amino acid sequence of SEQ ID NO: 2 whereby the polynucleotide is expressed and flowering time of the plant is delayed.

2. A method for controlling flowering time in plants, comprising transforming the plants with a recombinant vector comprising an isolated polynucleotide that encodes a COG protein controlling flowering in plants inserted in the sense direction wherein said COG protein has the amino acid sequence of SEQ ID NO: 2, and thus overexpressing a COG gene whereby the flowering time of the plants is delayed.

3. The method of claim 1, wherein the plants are selected from the group comprising rice, wheat, barley, corn, bean, red bean, potato, oat, millet, *Arabidopsis*, Chinese cabbage, radish, red pepper, strawberry, tomato, watermelon, cucumber, cabbage, melon, squash, stone-leek, onion, carrot, ginseng, tobacco, cotton, sesame, sugar cane, sugar beet, wild sesame, peanut, rape, apple, pear, date, peach, western Actinidia, grape, orange, persimmon, plum, apricot, banana, rose, gladiolus, gerbera, carnation, mum, lily, tulip, ryegrass, red clover, orchard grass, alfalfa, tall fescue and perennial ryegrass.

* * * * *